US008182414B2

(12) United States Patent
Handa et al.

(10) Patent No.: US 8,182,414 B2
(45) Date of Patent: May 22, 2012

(54) ENDOSCOPE SYSTEM HAVING RETAINING INSTRUMENT

(75) Inventors: Keiji Handa, Hachioji (JP); Hitoshi Karasawa, Hachioji (JP); Daisuke Asada, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1022 days.

(21) Appl. No.: 12/132,983

(22) Filed: Jun. 4, 2008

(65) Prior Publication Data
US 2008/0312499 A1 Dec. 18, 2008

(30) Foreign Application Priority Data

Jun. 14, 2007 (JP) ................................. 2007-157948

(51) Int. Cl.
*A61B 1/04* (2006.01)
(52) U.S. Cl. ......... 600/102; 600/103; 600/113; 600/160
(58) Field of Classification Search .................. 600/102, 600/103, 101, 113, 111, 166, 160, 173
See application file for complete search history.

(56) References Cited

U.S. PATENT DOCUMENTS

| 4,953,539 | A | * | 9/1990 | Nakamura et al. | ............. | 600/109 |
| 5,354,302 | A | * | 10/1994 | Ko | ................. | 606/104 |
| 5,494,483 | A | * | 2/1996 | Adair | ............................ | 600/111 |
| 5,653,677 | A | * | 8/1997 | Okada et al. | ................... | 600/112 |
| 7,001,329 | B2 | * | 2/2006 | Kobayashi et al. | ............ | 600/114 |
| 7,108,657 | B2 | * | 9/2006 | Irion et al. | .................... | 600/110 |
| 2002/0007110 | A1 | * | 1/2002 | Irion | .............................. | 600/170 |
| 2003/0004397 | A1 | * | 1/2003 | Kameya et al. | ................ | 600/101 |
| 2003/0135091 | A1 | * | 7/2003 | Nakazawa et al. | ............. | 600/113 |
| 2005/0075538 | A1 | * | 4/2005 | Banik et al. | ..................... | 600/141 |
| 2005/0090711 | A1 | * | 4/2005 | Fuchs et al. | ..................... | 600/113 |
| 2005/0165272 | A1 | * | 7/2005 | Okada et al. | ................... | 600/114 |
| 2006/0074307 | A1 | * | 4/2006 | Igarashi et al. | ................ | 600/434 |
| 2006/0149129 | A1 | * | 7/2006 | Watts et al. | ..................... | 600/113 |
| 2007/0049803 | A1 | * | 3/2007 | Moriyama | ..................... | 600/176 |
| 2007/0073102 | A1 | * | 3/2007 | Matsuno et al. | .............. | 600/102 |
| 2007/0161855 | A1 | * | 7/2007 | Mikkaichi et al. | ............. | 600/113 |

(Continued)

FOREIGN PATENT DOCUMENTS

JP 07-323002 12/1995

(Continued)

OTHER PUBLICATIONS

Chinese Office Action dated Oct. 16, 2009.

*Primary Examiner* — John P Leubecker
(74) *Attorney, Agent, or Firm* — Scully, Scott, Murphy & Presser, P.C.

(57) ABSTRACT

An endoscope system having a first image pickup device including at least one image pickup unit that is capable of picking up an image of an object, a second image pickup device including at least one image pickup unit, the second image pickup device being different from the first image pickup device, a retaining member being provided for retaining the second image pickup device in a body cavity, and including a camera cable that is connected to the second image pickup device and transmits an image pickup signal obtained by the second image pickup device, and a wire connected to the second image pickup device, a signal processing device that is provided outside the body cavity and processes image pickup signals obtained by the first image pickup device and the second image pickup device, and a display device that displays an image signal outputted from the signal processing device.

6 Claims, 8 Drawing Sheets

U.S. PATENT DOCUMENTS

| | | |
|---|---|---|
| 2007/0225573 A1 * | 9/2007 | Stokes et al. .................. 600/249 |
| 2007/0232863 A1 * | 10/2007 | Miyake et al. ................. 600/204 |
| 2007/0255100 A1 * | 11/2007 | Barlow et al. ................. 600/114 |

FOREIGN PATENT DOCUMENTS

| | | |
|---|---|---|
| JP | 10-108824 | 4/1998 |
| JP | 2000-032442 | 1/2000 |
| JP | 2004-041580 | 2/2004 |
| JP | 2005-204806 | 8/2005 |
| JP | 2006-149846 | 6/2006 |
| WO | WO 2007/007842 A1 | 1/2007 |
| WO | 2007/061386 | 5/2007 |

* cited by examiner

ENDOSCOPE SYSTEM HAVING RETAINING INSTRUMENT

CROSS REFERENCE TO RELATED APPLICATION

This application claims benefit of Japanese Patent Application No. 2007-157948 filed on Jun. 14, 2007, the contents of which are incorporated by this reference.

BACKGROUND OF THE INVENTION

1. Field of the Invention

The present invention relates to an endoscope system that can extensively view the inside of an abdominal cavity and includes an image pickup device fixed on an inner side of the abdominal cavity.

2. Description of the Related Art

In recent years, a surgical operation for, without dissecting the abdomen of a patient in order to reduce invasion to a patient, penetrating, into the abdomen, a trocar that leads an endoscope for observation into a body cavity and a trocar that leads a treatment instrument to a treatment region and performing treatment while observing the treatment instrument and the treatment region with the endoscope, a so-called laparoscopic surgical operation, has been performed. With this method, a range of a visual field that can be actually observed by the endoscope is relatively narrow. Therefore, since it is difficult to extensively observe the entire treatment region in the abdominal cavity, it is difficult to accurately grasp, for example, a positional relation between the treatment instrument and organs.

In order to solve this problem, for example, Japanese Patent Application Laid-Open Publication No. 2004-41580 discloses a wide-angle observation device including, separately from respective operation units, an observation device that is inserted into a body wall and can observe a wide-angle visual field.

For example, Japanese Patent Application Laid-Open Publication No. 2000-32442 discloses an endoscope system including plural scopes, which are respectively inserted to an observation object region in an abdominal wall via plural trocars penetrated into the abdominal wall.

SUMMARY OF THE INVENTION

An endoscope system according to the present invention includes at least one first photographing device that can photograph an object, at least one second photographing device different from the first photographing device, a retaining member for retaining the second photographing device in a body cavity, a signal processing device that processes signals photographed by the first photographing device and the second photographing device, and a display device that displays an image signal outputted from the signal processing device.

The above and other objects, feature and advantages of the invention will become more clearly understood from the following description referring to the accompanying drawings.

DETAILED DESCRIPTION OF THE PREFERRED EMBODIMENTS

Embodiments of the present invention will be hereinafter explained with reference to the accompanying drawings.

(First Embodiment)

Figure 1:
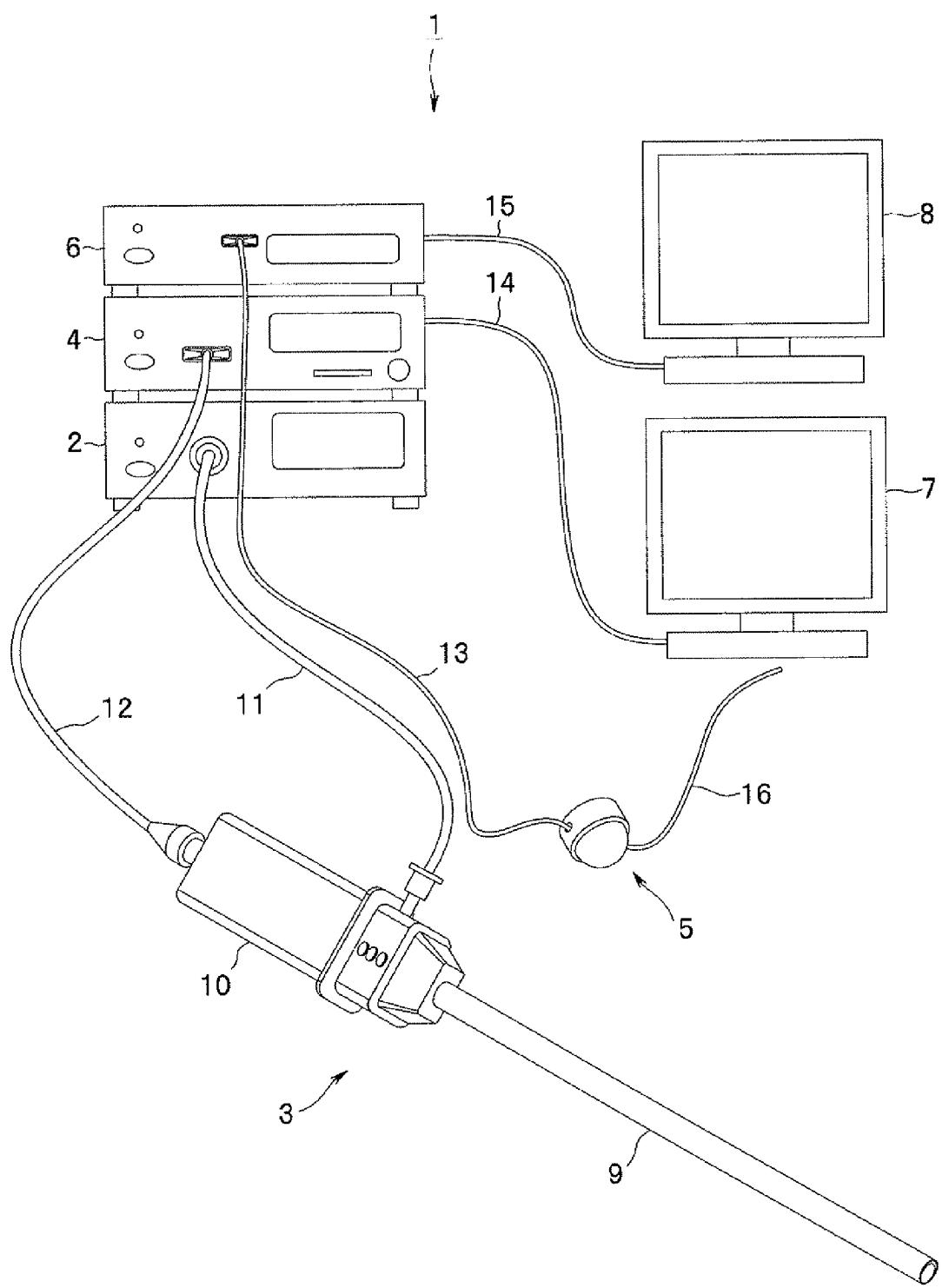
FIG. 1 is a diagram showing a configuration of an endoscope system according to a first embodiment of the present invention.
Figure 2:
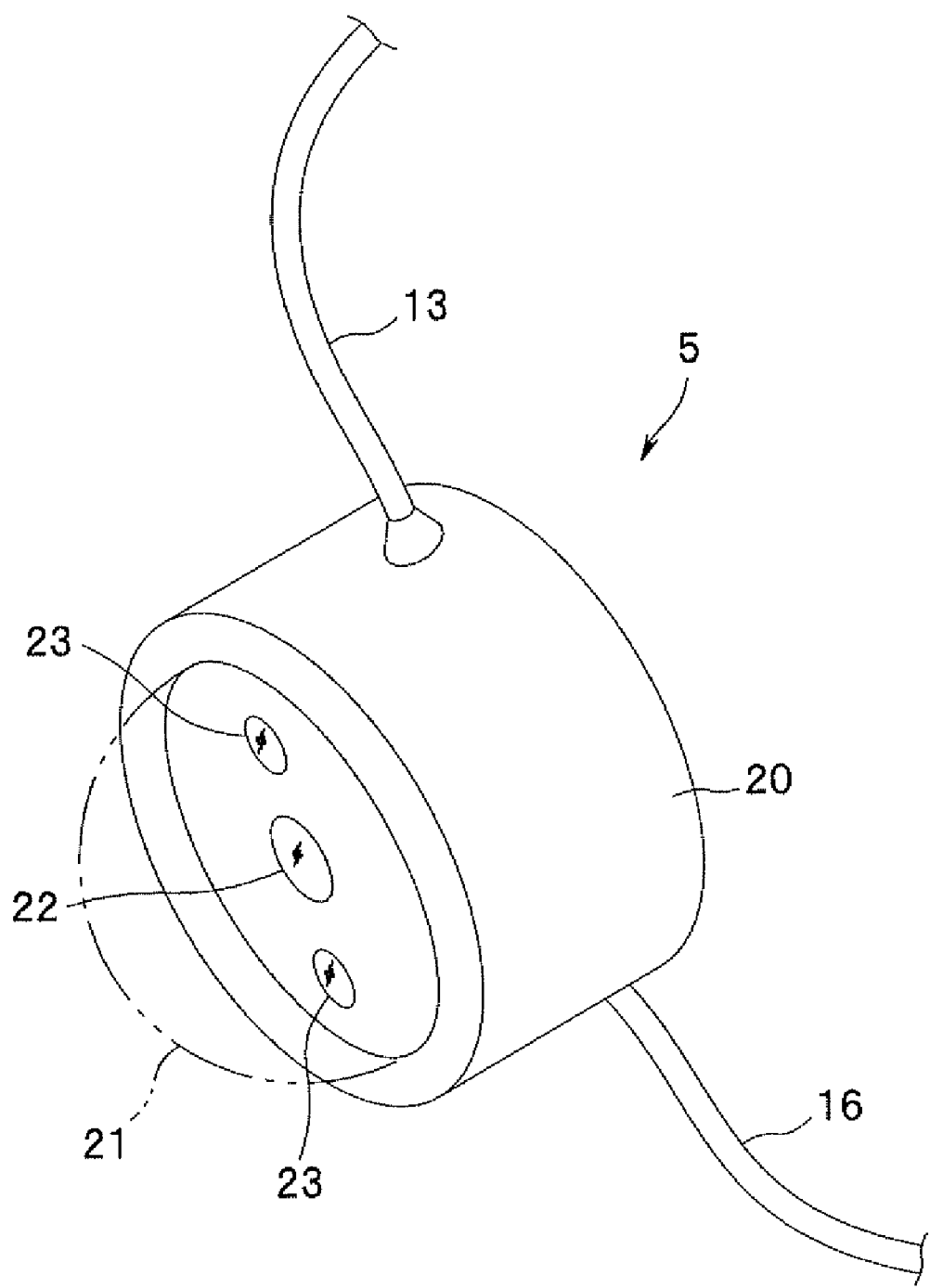
FIG. 2 is a perspective view showing a configuration of an intra-body cavity set camera according to the first embodiment of the present invention.
Figure 3:
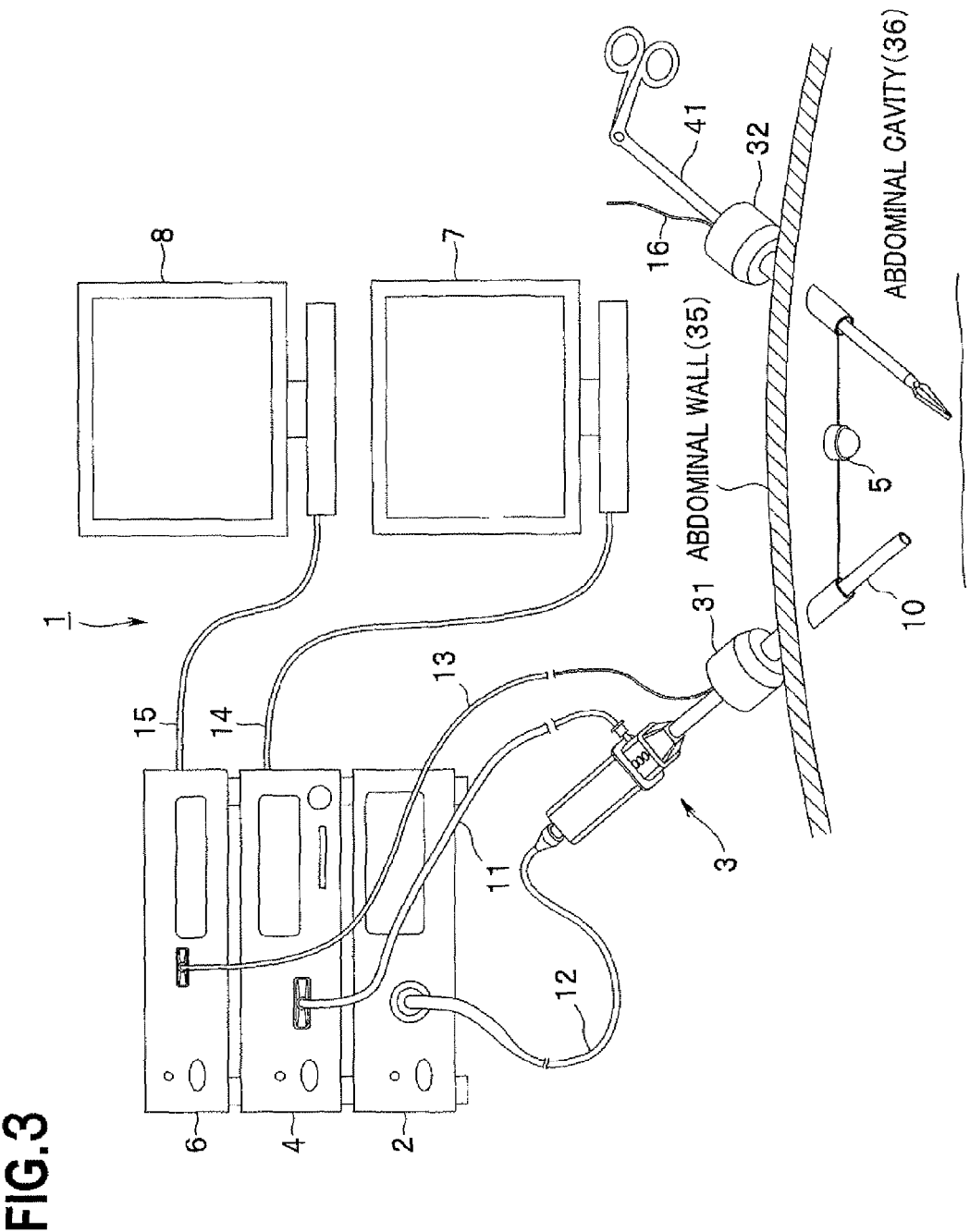
FIG. 3 is a diagram showing a state in which the endoscope system according to the first embodiment of the present invention is set on a patient.
Figure 8:
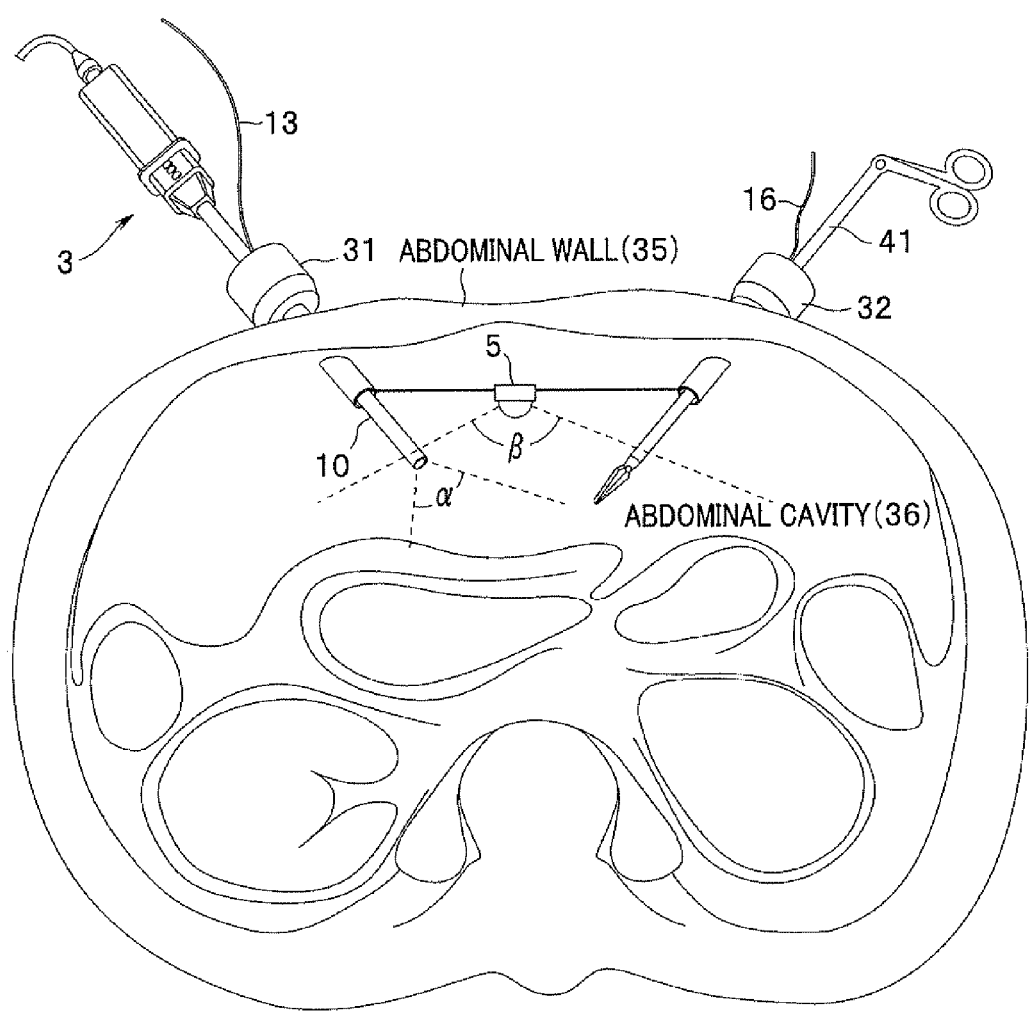
FIG. 8 is a diagram showing view angles of a rigid endoscope and the intra-body cavity set camera according to the first embodiment of the present invention set in the body cavity.

First, an endoscope system according to a first embodiment of the present invention is explained below. FIGS. 1 to 8 relate to the first embodiment of the present invention. FIG. 1 is a diagram showing a configuration of the endoscope system. FIG. 2 is a perspective view showing a configuration of an intra-body cavity set camera. FIG. 3 is a diagram showing a state in which the endoscope system is set on a patient. FIGS. 4 to 7 are diagrams for explaining a procedure for leading the intra-body cavity set camera into a body cavity. FIG. 8 is a diagram showing view angles of a rigid endoscope and the intra-body cavity set camera set in the body cavity.

As shown in FIG. 1, an endoscope system I according to the present embodiment for performing a laparoscopic surgical operation mainly includes a light source device 2, a rigid endoscope 3 as a first photographing device, a first camera control unit (hereinafter abbreviated as CCU) 4 as a first signal processing device, an extremely small intra-body cavity set camera (hereinafter abbreviated as camera) 5 as a second photographing device, a second CCU 6 as a second signal processing device, a first display device 7, and a second display device 8.

The light source device 2 supplies illumination light to an illumination optical system included in the rigid endoscope 3. The light source device 2 and the rigid endoscope 3 are detachably connected by a light source cable 11.

The rigid endoscope 3 mainly includes a rigid inserting section 9 and an operation section 10 coupled to a proximal end of the inserting section 9.

In the inserting section 9 of the rigid endoscope 3, an image guide and a light guide bundle are inserted. On a distal end surface thereof, a photographing optical system that collects light of a subject image in a rigid endoscope camera described later via the image guide and an illumination optical system that radiates illumination light from the light guide bundle to the subject are disposed.

A not-shown rigid endoscope camera is built in the operation section of the rigid endoscope 3. An optical image in an observation region illuminated by illumination light supplied from the light source device 2 to the rigid endoscope 3 through the light source cable 11 is picked up by the rigid endoscope camera of the operation section 10 via the image guide of the inserting section 9. The rigid endoscope camera photoelectrically converts the picked-up optical image into an image signal. The image signal is transmitted to the first CCU 4 through an image pickup cable 12.

The first CCU 4 generates a video signal from the transmitted image signal and outputs the video signal to the first display device 7. The first display device 7 is, for example, a liquid crystal display. The first display device 7 receives the video signal outputted from the first CCU 4 and displays an endoscope image of the observation region on a screen.

In the rigid endoscope 3 according to the present embodiment, an image pickup optical system is set such that an angle of view a (see FIG. 8), which is a photographable angle of the rigid endoscope 3, is in a range of, for example, 70° to 75°.

As shown in FIGS. 1 and 2, the camera 5 includes a camera main body 20 of a substantially columnar shape and a transparent hood 21 of a substantially dome shape disposed on one end face of the camera main body 20.

One end of a camera cable 13 is extended out from a side peripheral surface of the camera main body 20. The other end of the camera cable 13 is connected to the second CCU 6 by a connector. A wire 16 is extended out from a position on an opposite side of a side peripheral portion that is point-symmetrical to a substantial center of the camera main body 20 from which the camera cable 13 is extended out.

The camera main body 20 includes an image pickup unit, an illuminating unit a control unit and a power supply unit, which are not shown in the figure. The image pickup unit built in the camera main body 20 is an image pickup device such as a CCD and a C-MOS. The image pickup unit picks up an optical image of an observation region illuminated by illumination light of the illuminating unit including a white LED built therein.

On one end face of the camera main body 20 on which the transparent hood 21 is disposed, an image pickup window 22 and illumination windows 23 are provided. In a substantial center of the image pickup window 22, an image pickup optical system for collecting photographing light using the image pickup unit is disposed. The illumination windows 23 are arranged around the image pickup window 22. In the illumination windows 23, illumination optical systems for emitting the illumination light from the illuminating unit to a subject are arranged.

In the present embodiment, an image signal outputted from a transmitting and receiving unit is transmitted to the second CCU 6 through a signal line inserted through the camera cable 13. The second CCU 6 generates a video signal from the transmitted image signal and outputs the video signal to the second display device 8. The second display device 8 is also a liquid crystal display. The second display device 8 receives the video signal outputted from the second CCU 6 and displays a camera image on a screen.

In the camera 5 according to the present embodiment, the image pickup optical system is set such that an angle of view β (see FIG. 8), which is a photographable angle of the camera 5, is a view angle wider than that of the rigid endoscope 3, for example, a view angle equal to or larger than 90°.

In FIG. 1, reference numeral 14 denotes a first video cable and reference numeral 15 denotes a second video cable. The first video cable 14 connects the first CCU 4 and the first display device 7. The second video cable 15 connects the second CCU 6 and the second display device 8.

The endoscope system 1 according to the present embodiment configured as described above is used for the laparoscopic surgical operation and used for, as shown in FIG. 3, treatment in an abdominal cavity of a patient.

A procedure for setting, for the laparoscopic surgical operation, the endoscope system 1 according to the present embodiment in an abdominal cavity, i.e., a body cavity, of a patient is explained below with reference to FIGS. 3 to 7.

Figure 4:
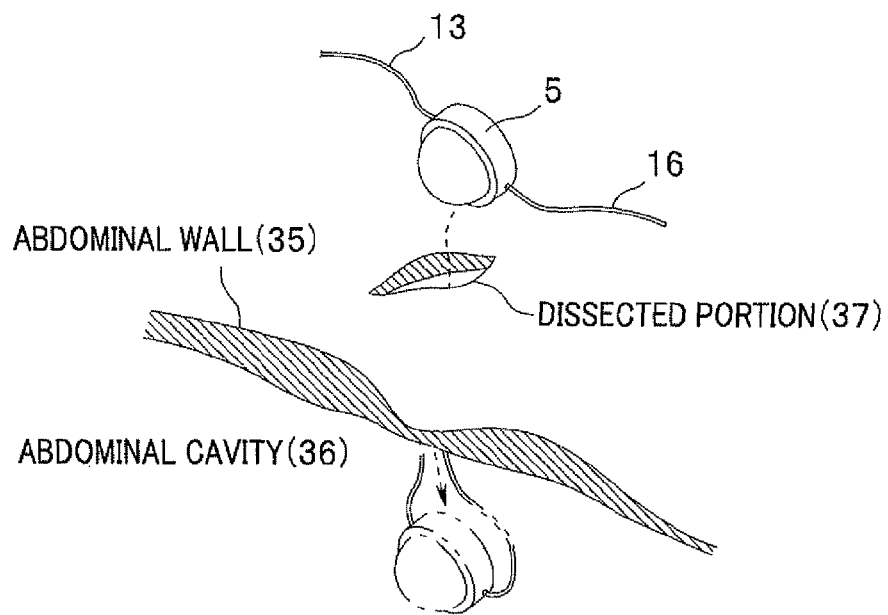
FIG. 4 is a first diagram for explaining a procedure for leading the intra-body cavity set camera according to the first embodiment of the present invention into a body cavity.

First, as shown in FIG. 4, a surgeon forms a dissected portion 37 with a knife or the like in an abdominal wall 35 of the patient in order to penetrate a trocar 31. The surgeon leads the camera 5 into an abdominal cavity 36 from the dissected portion 37. At this point, the surgeon also leads the wire 16 into the abdominal cavity 36 together with the camera 5 and does not completely lead the camera cable 13 into the abdominal cavity 36.

Figure 5:
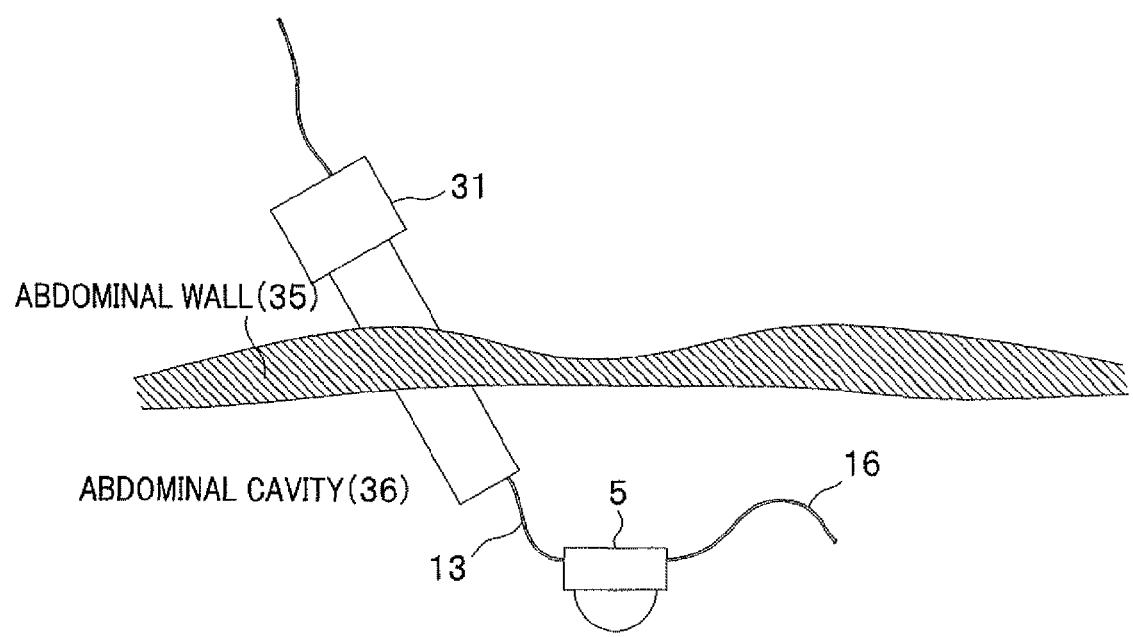
FIG. 5 is a second diagram for explaining the procedure for leading the intra-body cavity set camera according to the first embodiment of the present invention into the body cavity.

The surgeon inserts the camera cable 13 into an insertion hole of the trocar 31 from a distal end opening. As shown in FIG. 5, the surgeon penetrates the trocar 31 into the abdominal cavity 36 from the dissected portion 37.

Next, in another place a predetermined distance apart from the trocar 31, the surgeon dissects the abdominal wall 35 and penetrates, into the abdominal cavity 36, a trocar 32 for leading a treatment instrument 41 such as grasping forceps into the abdominal cavity 36.

Figure 6:
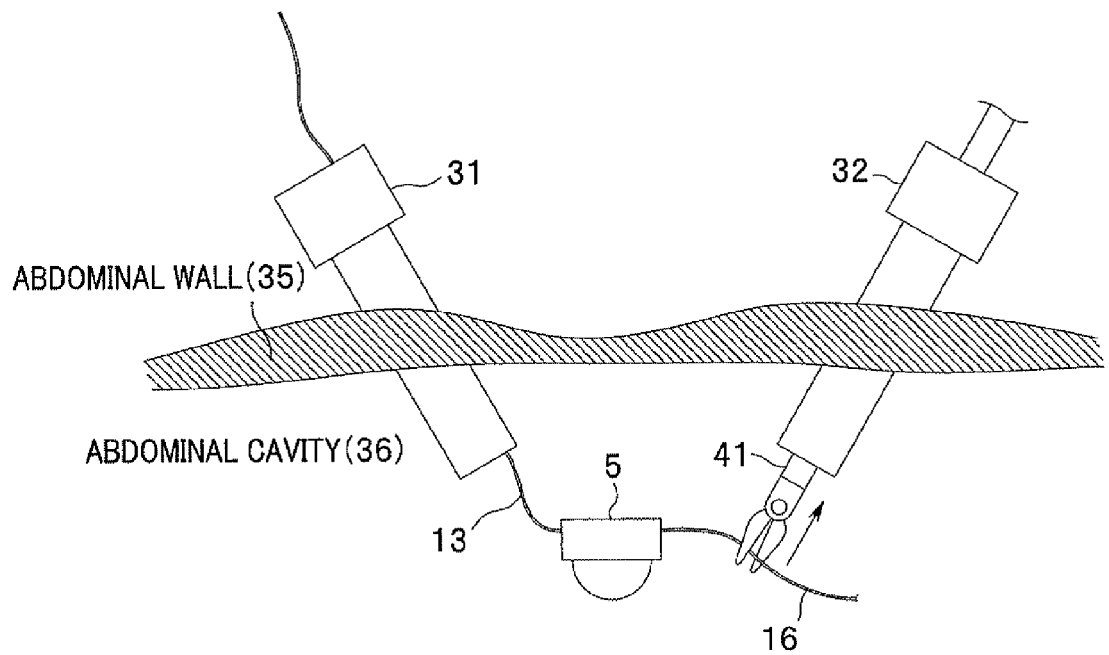
FIG. 6 is a third diagram for explaining the procedure for leading the intra-body cavity set camera according to the first embodiment of the present invention into the body cavity.
Figure 7:
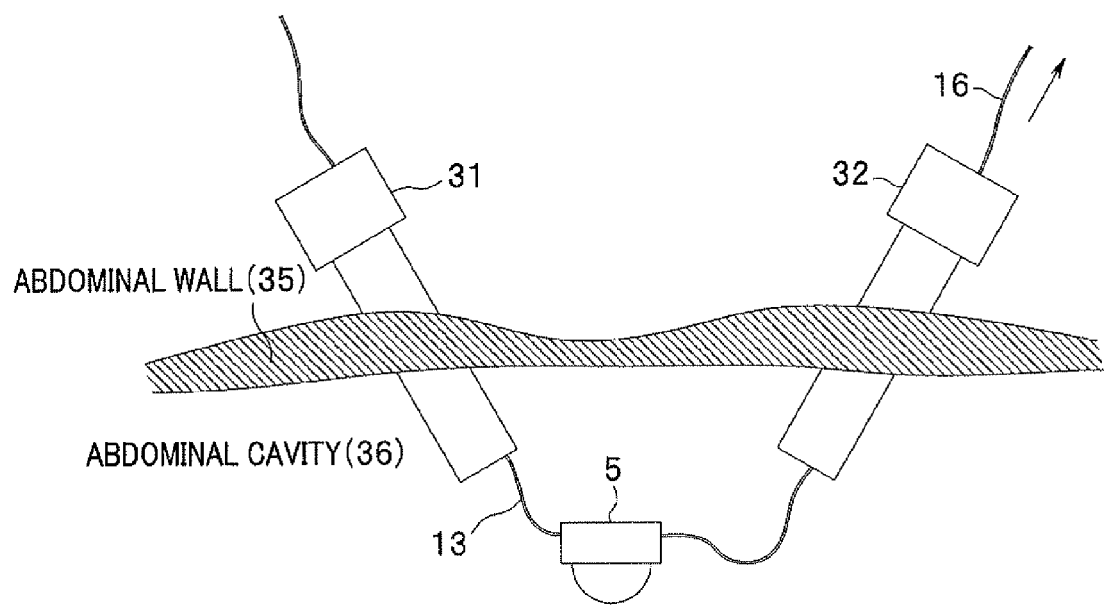
FIG. 7 is a fourth diagram for explaining the procedure for leading the intra-body cavity set camera according to the first embodiment of the present invention into the body cavity.

As shown in FIG. 6, the surgeon pulls up the treatment instrument 41 such as grasping forceps in a state in which the wire 16 extending out from the camera 5 is grasped by the treatment instrument 41 and pulls the wire 16 to the outside of the abdominal cavity 36 through an insertion hole of the trocar 32. At this point, it is advisable that the surgeon leads the rigid endoscope 3 into the abdominal cavity 36 via the trocar 31 and, while observing an image photographed by the rigid endoscope 3, grasps the wire 16 with the treatment instrument 41 and pulls the wire 16 to the outside of the abdominal cavity 36.

The surgeon retains the camera 5 in a desired observation position in the abdominal cavity 36 by applying predetermined tension to the camera 5 while tugging and loosening the camera cable 13 and the wire 16. At this point, the surgeon fixes the camera cable 13 and the wire 16 to the trocars 31 and 32 using a tape, a locking member, or the like while keeping applying the predetermined tension thereto. In other words, as shown in FIGS. 3 and 8, the camera 5 is lifted to the abdominal wall 35 side by the tension of the camera cable 13 and the wire 16.

For example, one end of a not-shown aeroperitoneum tube is attached to the trocar 31. For example, carbon dioxide gas or the like is injected into the abdominal cavity 36 as gas for aeroperitoneum for the purpose of securing a visual field of the rigid endoscope 3 and for the purpose of securing an area for operating operation equipment and the like. In the state in which the camera 5 is retained in the abdominal cavity 36, the surgeon inserts the rigid endoscope 3 through the trocar 31 and inserts the treatment instrument 41 through the trocar 32 and performs the laparoscopic surgical operation.

As explained above, with the endoscope system 1 according to the present embodiment, only two penetration holes as dissected portions for leading the trocar 31, which leads the rigid endoscope 3 into the abdominal cavity 36, and the trocar 32, which leads the treatment instrument 41 into the abdominal cavity 36 have to be formed in the abdominal wall 35 as shown in FIG. 8.

When the camera 5 is led into the abdominal cavity 36, the dissected portion 37 for leading the trocar 31 into the abdominal cavity 36 is used. Therefore, with the endoscope system 1 according to the present embodiment, the laparoscopic surgical operation with low invasion can be provided to the patient as before.

In the endoscope system 1 according to the present embodiment, the angle of view β as a view angle of the camera 5 is set to be wider than the angle of view a as a view angle of the rigid endoscope 3 (α<β). Therefore, with the endoscope system 1, the laparoscopic surgical operation is performed using the rigid endoscope 3 having a relatively narrow range of a visual field and the camera 5 that can extensively observe an entire treatment region in an abdominal cavity. Consequently, the endoscope system 1 provides improved operability and has high visibility for the surgeon.

In the endoscope system 1, the camera 5 has only to be lifted to the abdominal wall 35 side in the abdominal cavity 36 and retained by the tension of the camera cable 13 and the wire 16 forming the retaining member. Therefore, treatment for retaining the camera 5 is not complicated and can be performed relatively easily.

(Second Embodiment)

Figure 9:
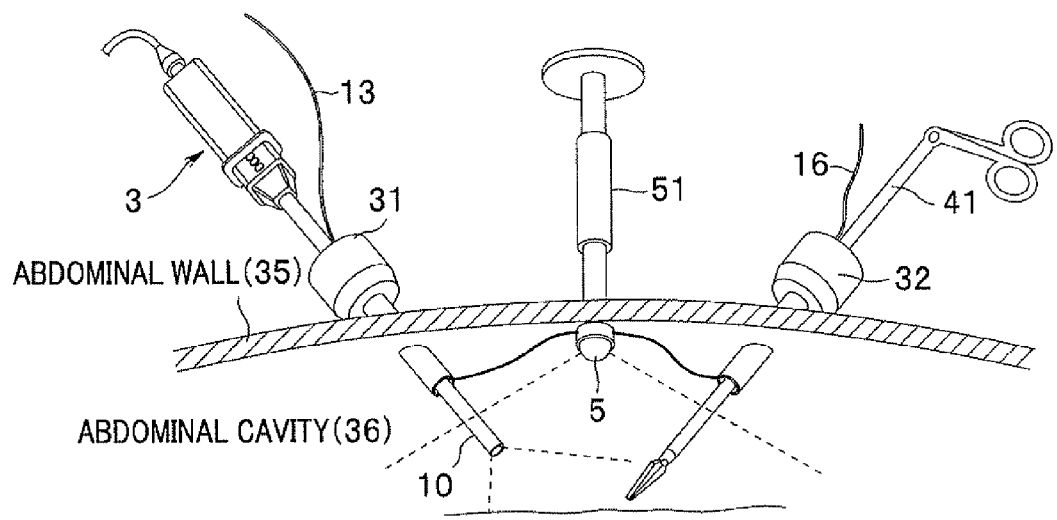
FIG. 9 is a diagram showing a state in which an endoscope system according to a second embodiment of the present invention is set on a patient.
Figure 10:
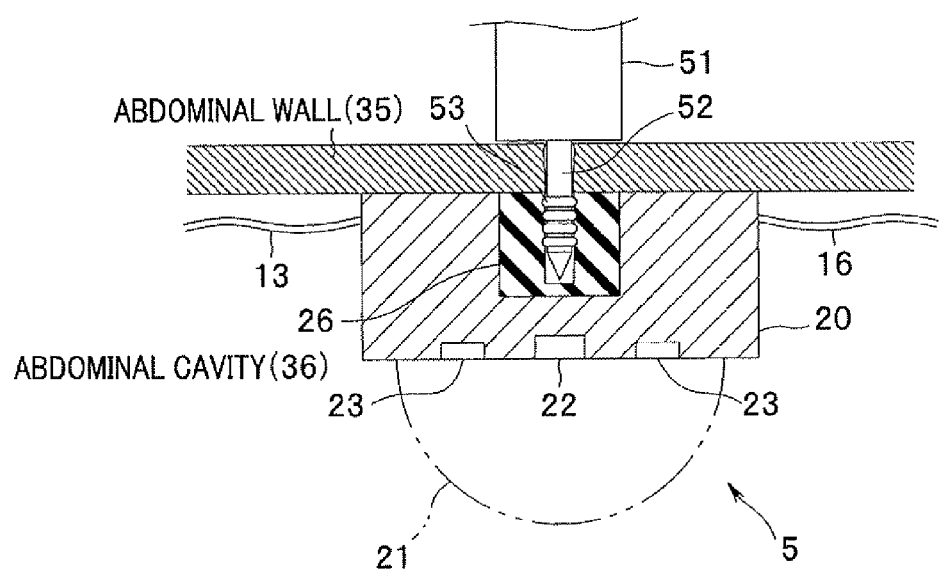
FIG. 10 is a sectional view showing a state in which an intra-body cavity set camera according to a second embodiment of the present invention is fixed by an abdominal cavity needle through an abdominal wall.

An endoscope system according to a second embodiment of the present invention is explained below with reference to FIGS. 9 and 10. FIGS. 9 and 10 relate to the second embodiment of the present invention. FIG. 9 is a diagram showing a state in which the endoscope system is set on a patient. FIG. 10 is a sectional view showing a state in which an intra-body cavity set camera is fixed by an abdominal cavity needle through an abdominal wall. In the following explanation, components identical with those of the endoscope system 1 according to the first embodiment are denoted by the same reference numerals. Detailed explanation of the components is omitted.

As shown in FIG. 9, the endoscope system 1 according to the present embodiment includes an abdominal cavity needle 51 that is a retaining instrument for fixing and retaining the camera 5 on an inner surface of the abdominal wall 35. As shown in FIG. 10, the abdominal cavity needle 51 includes a needle section 52 projected from a distal end thereof and plural concave sections 53 provided over the entire outer periphery of the needle section 52.

In the camera 5 according to the present embodiment, an elastic member 26 having a hole in which the needle section 52 of the abdominal cavity needle 51 is penetrated is disposed from a substantial center of one end face on the opposite side of the other end face of the camera main body 20, on which the image pickup window 22 and the illumination windows 23 are disposed, to the inside of the camera 5. Therefore, in the camera 5, the needle section 52 of the abdominal cavity needle 51 is penetrated into the elastic member 26 and the plural concave sections 53 provided in the needle section 52 are surely locked in the hole of the elastic member 26 by an elastic force.

In the endoscope system 1 according to the present embodiment described above, the camera 5 can be fixed on the inner surface of the abdominal wall 35. Therefore, it is possible to retain the camera 5 in the abdominal cavity 36 in a stable state. With the endoscope system 1, since the abdominal cavity needle 51 is used, it is unnecessary to dissect the abdominal wall 35 and the needle section 52 of the abdominal cavity needle 51 has only to be simply penetrated into the abdominal wall 35. Therefore, the endoscope system 1 does not apply a heavy load to a patient. Other actions and effects are the same as those in the first embodiment.

(Third Embodiment)

Figure 11:
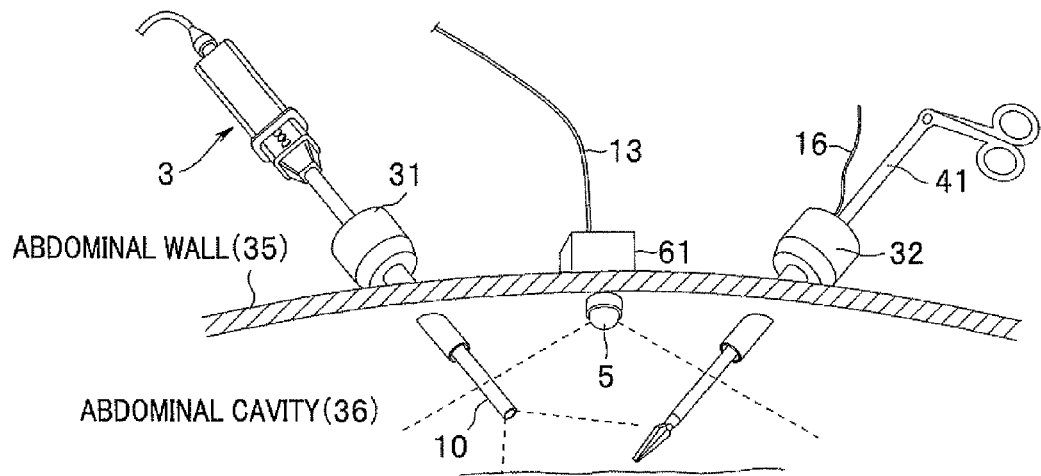
FIG. 11 is a diagram showing a state in which an endoscope system according to a third embodiment of the present invention is set on a patient.
Figure 12:
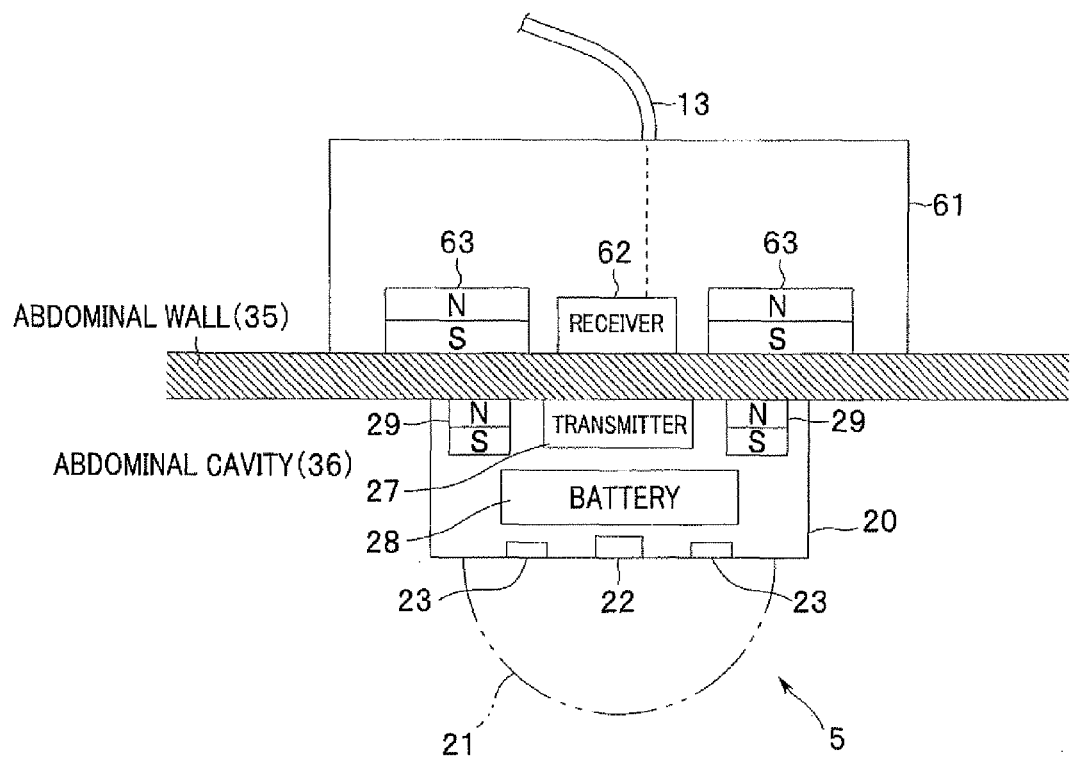
FIG. 12 is a block diagram showing a state in which an intra-body cavity set camera and a receiving device according to a third embodiment of the present invention are fixed by a magnetic force through an abdominal wall.

An endoscope system according to a third embodiment of the present invention is explained below with reference to FIGS. 11 and 12. FIGS. 11 and 12 relate to the third embodiment of the present invention. FIG. 11 is a diagram showing a state in which the endoscope system is set on a patient. FIG. 12 is a block diagram showing a state in which an intra-body cavity set camera and a receiving device are fixed by a magnetic force through an abdominal wall. In the following explanation, as in the above explanation, components identical with those of the endoscope system 1 according to the first embodiment are denoted by the same reference numerals. Detailed explanation of the components is omitted.

The endoscope system 1 according to the present embodiment transits an image of the inside of the abdominal cavity 36 photographed by the camera 5 to the outside of the abdominal cavity 36 by radio. Specifically, as shown in FIG. 11, the camera 5 according to the present embodiment does not include a communication cable for transmitting an image signal to the outside of the abdominal cavity 36 and transmits the image signal by radio to a receiving device 61 placed on a surface skin of the abdominal wall 35.

Therefore, the camera cable 13 is connected to the receiving device 61. The receiving device 61 receives a video signal photographed by the camera 5 and outputs the video signal to the second CCU 6 (see FIG. 1) through the camera cable 13.

A configuration of the camera 5 is explained in detail. As shown in FIG. 12, the camera main body 20 of the camera 5 includes a transmitter 27, a battery 28 that supplies electric power to the transmitter 27, an image pickup device, an illumination device, and a control circuit, which are not shown in the figure, and plural internal magnets 29. The receiving device 61 includes a receiver 62 and plural external magnets 63.

The transmitter 27 of the camera 5 transmits an image signal photoelectrically converted by the image pickup device to the receiver 62 of the receiving device 61. The receiver 62 of the receiving device 61 receives the image signal and outputs the image signal to the second CCU 6 through the camera cable 13.

In the endoscope system 1 according to the present embodiment, in a state in which the abdominal wall 35 is sandwiched between the camera 5 and the receiving device 61, the camera 5 is attracted to the receiving device 61 which is placed on the surface skin of the abdominal wall 35, and fixed and retained on the inner surface of the abdominal wall 35 by magnetic forces of the internal magnets 29 provided in the camera 5 and the external magnets 63 provided in the receiving device 61.

In the endoscope system 1 according to the present embodiment described above, as in the second embodiment, the camera 5 can be fixed on the inner surface of the abdominal wall 35. Therefore, the camera 5 can be retained in the abdominal cavity 36 in a stable state. Other actions and effects are the same as those in the first embodiment.

In the embodiments explained above, the rigid endoscope 3 and the image pickup device of the camera 5 are provided on the premise that photographing is performed under ordinary light. However, the present invention is not limited thereto.

When infrared image pickup devices are used as the rigid endoscope 3 and the image pickup device of the camera 5, the illumination devices are not necessary. As a result, it is possible to reduce sizes of the rigid endoscope 3 and the camera 5.

It is possible to easily observe blood vessels hidden in fat tissues in the abdominal cavity 36 by changing illumination light from the illumination devices to infrared rays. Consequently, for example, in large bowel resection, if the image pickup device can perform infrared observation, it is easy to ablate plural arterial vessels connected to the large intestine.

With the endoscope system 1 according to the embodiments described above, it is possible to observe internal tissues in the body cavity, i.e., the abdominal cavity 36 from multiple viewpoints including a wide angle. For example, it is possible to easily observe an ablation line in an operation of a large organ or ablation of the large intestine. Therefore, it is possible to make it easy to perform treatment of the laparoscopic surgical operation by using the endoscope system 1 according to the embodiments of the present invention.

The invention described in the embodiments is not limited to the embodiments and modifications thereof. Besides, it is possible to carry out various modifications without departing from the sprit of the invention at an implementation stage. Moreover, inventions at various stages are included in the embodiments. Various inventions can be extracted by appropriate combinations in the disclosed plural components.

For example, even if several components are deleted from all the components described in the embodiments, when the problems described above can be solved and the effects described above can be obtained, a configuration obtained by deleting the components can be extracted as an invention.

Having described the embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope system comprising:
    a first image pickup device including at least one image pickup unit that is capable of picking up an image of an object;
    a second image pickup device including at least one image pickup unit, the second image pickup device being different from the first image pickup device;
    a retaining instrument being provided for retaining the second image pickup device in a body cavity, the retaining instrument including a camera cable that is connected to the second image pickup device and transmits an image pickup signal obtained by the second image pickup device, and a wire connected to the second image pickup device;
    a signal processing device that is provided outside the body cavity and processes image pickup signals obtained by the first image pickup device and the second image pickup device;
    a display device that displays an image signal outputted from the signal processing device, and
    a fixing device for fixing the second image pickup device on an inner surface of a body wall, the fixing device including a needle section for penetration from an outside of the body cavity,
    wherein the second image pickup device has a hole, and the second image pickup device is fixed to the body wall by engagement of the needle section and the hole.

2. The endoscope system according to claim 1, wherein the first image pickup device and the second image pickup device are capable of being controlled from an outside of the body cavity.

3. The endoscope system according to claim 2, further comprising
    a trocar configured to pierce through a body wall,
    wherein the camera cable which transmits the image pickup signal obtained by the second image pickup device is connected to the signal processing device provided outside of the body cavity through an insertion hole of the trocar.

4. The endoscope system according to claim 1, wherein the second image pickup device is capable of picking up an image at a view angle wider than that of the first image pickup device.

5. The endoscope system according to claim 1, further comprising:
    a trocar configured to pierce through a body wall,
    wherein the camera cable which transmits the image pickup signal obtained by the second image pickup device is connected to the signal processing device provided outside of the body cavity through an insertion hole of the trocar.

6. The endoscope system according to claim 1, wherein the second image pickup device has an illumination unit, and the illumination unit emits infrared illumination light.

* * * * *